US008592201B2

(12) United States Patent
Story et al.

(10) Patent No.: US 8,592,201 B2
(45) Date of Patent: Nov. 26, 2013

(54) CHONDROCYTE CONTAINER AND METHOD OF USE

(75) Inventors: Brooks J. Story, Franklin, MA (US); Francois Binette, San Francisco, CA (US); M. E. Liesbeth Brown, West Newton, MA (US)

(73) Assignee: DePuy Mitek, LLC

( * ) Notice: Subject to any disclaimer, the term of this patent is extended or adjusted under 35 U.S.C. 154(b) by 0 days.

(21) Appl. No.: 13/567,322

(22) Filed: Aug. 6, 2012

(65) Prior Publication Data

US 2012/0302958 A1 Nov. 29, 2012

Related U.S. Application Data

(62) Division of application No. 12/123,650, filed on May 20, 2008, now Pat. No. 8,257,963.

(60) Provisional application No. 60/941,326, filed on Jun. 1, 2007.

(51) Int. Cl.

| | |
|---|---|
| *C12M 1/00* | (2006.01) |
| *C12M 1/36* | (2006.01) |
| *C12M 1/38* | (2006.01) |
| *C12M 1/12* | (2006.01) |
| *C12N 5/00* | (2006.01) |

(52) U.S. Cl.

USPC .................. 435/286.5; 435/283.1; 435/286.2; 435/297.1; 435/325

(58) Field of Classification Search

USPC .............. 435/283.1, 286.2, 286.5, 297.1, 325

See application file for complete search history.

(56) References Cited

U.S. PATENT DOCUMENTS

| | | | | |
|---|---|---|---|---|
| 4,105,034 | A | | 8/1978 | Shalaby et al. |
| 4,130,639 | A | | 12/1978 | Shalaby et al. |
| 4,140,678 | A | | 2/1979 | Shalaby et al. |
| 4,141,087 | A | | 2/1979 | Shalaby et al. |
| 4,205,399 | A | | 6/1980 | Shalaby et al. |
| 4,208,511 | A | | 6/1980 | Shalaby et al. |
| 4,332,255 | A | | 6/1982 | Hakim et al. |
| 4,352,883 | A | | 10/1982 | Lim |
| 4,373,527 | A | | 2/1983 | Fischell |
| 4,387,715 | A | | 6/1983 | Hakim et al. |
| 4,551,128 | A | | 11/1985 | Hakim et al. |
| 4,595,390 | A | | 6/1986 | Hakim et al. |
| 4,615,691 | A | | 10/1986 | Hakim et al. |
| 4,642,120 | A | | 2/1987 | Nevo et al. |
| 4,904,259 | A | | 2/1990 | Itay |
| 5,041,138 | A | | 8/1991 | Vacanti et al. |
| 5,053,050 | A | | 10/1991 | Itay |
| 5,108,753 | A | | 4/1992 | Kuberasampath et al. |
| 5,283,187 | A | | 2/1994 | Aebischer et al. |
| 5,464,929 | A | | 11/1995 | Bezwada et al. |
| 5,468,253 | A | | 11/1995 | Bezwada et al. |
| 5,554,148 | A | | 9/1996 | Aebischer et al. |
| 5,595,751 | A | | 1/1997 | Bezwada et al. |
| 5,597,579 | A | | 1/1997 | Bezwada et al. |
| 5,607,687 | A | | 3/1997 | Bezwada et al. |
| 5,618,552 | A | | 4/1997 | Bezwada et al. |
| 5,620,698 | A | | 4/1997 | Bezwada et al. |
| 5,645,850 | A | | 7/1997 | Bezwada et al. |
| 5,648,088 | A | | 7/1997 | Bezwada et al. |
| 5,698,213 | A | | 12/1997 | Jamiolkowski et al. |
| 5,700,583 | A | | 12/1997 | Jamiolkowski et al. |
| 5,773,286 | A | * | 6/1998 | Dionne et al. ............ 435/297.1 |
| 5,842,477 | A | | 12/1998 | Naughton et al. |
| 5,855,619 | A | | 1/1999 | Caplan et al. |
| 5,859,150 | A | | 1/1999 | Jamiolkowski et al. |
| 5,869,041 | A | | 2/1999 | Vandenburgh |
| 5,872,094 | A | | 2/1999 | Goetinck et al. |
| 5,902,745 | A | | 5/1999 | Butler et al. |
| 5,939,323 | A | | 8/1999 | Valentini et al. |
| 5,968,502 | A | | 10/1999 | Treco et al. |
| 5,980,508 | A | | 11/1999 | Cardamone et al. |
| 6,001,352 | A | | 12/1999 | Boyan et al. |
| 6,008,013 | A | | 12/1999 | Reynolds |
| 6,013,853 | A | | 1/2000 | Athanasiou et al. |
| 6,048,729 | A | | 4/2000 | Selden et al. |
| 6,054,288 | A | | 4/2000 | Selden et al. |
| 6,103,528 | A | | 8/2000 | An et al. |

(Continued)

FOREIGN PATENT DOCUMENTS

| | | |
|---|---|---|
| AU | 2004205266 A1 | 3/2005 |
| CA | 2477164 A1 | 2/2005 |

(Continued)

OTHER PUBLICATIONS

Pacifici et. al., (1991) Exp. Cell Res. 195: 38-46.
Palmer et. al., (1983) Science, 222: 1337-1339.
Roark et. al., (1994) Develop. Dynam., 200: 103-116.
Rosselot et. al., (1994) J. Bone Miner. Res., 9: 431-439.
Salgaller et. al., (1998) J. Surg. Oncol., 68: 122.
Schwartz et. al., (1989) J. Bone Miner. Res. 4: 199-207.
Shapiro et. al., (1994) J. Bone Min. Res., 9: 1229-1237.
Smith et. al., (1993) Neuroscience 52: 7-16.
Steinert et al. "Arthritis Research & Therapy," 2007, vol. 9. No. 213, pp. 1-15.
Suda, (1985) Calcif Tissue Int., 37: 82-90.
Sullivan et. al., (1994) J. Biol. Chem., 269: 22500-22506.
Takaori-Kondo et. al., (1998) Blood, 91: 4747.
Uludag et al. (Advanced Drug Delivery Reviews. 2000; 42: 29-64).
Verma et al., Gene therapy: twenty-first century medicine. Annu Rev Biochem. 2005;74:711-38.
Wong et. al., (1999) Curr. Opin. Immunol., 11: 643-647.
Yokoo, Naoki, et al., J. Jpn. Orthop. Assoc., 2002, vol. 76, No. 8, p. S946.

(Continued)

*Primary Examiner* — Shin-Lin Chen

(57) ABSTRACT

Devices and methods for delivering a therapeutic agent produced via a genetically-altered chondrocyte are provided. More specifically, the device includes a housing which defines a cell chamber configured to retain a large volume of chondrocytes while selectively releasing therapeutic agents produced via these entrapped cells. In an exemplary embodiment, the cell chamber can be configured such that a portion of cells can be positioned at least about 1.5 mm from an external wall of the device (i.e., about 1.5 mm away from an external nutrient supply). For example, the cell chamber can have a tubular configuration having a length and a diameter wherein each of these dimensions is at least about 3 mm (thereby the central core to the chamber is at least about 1.5 mm from the outer wall of the device).

17 Claims, 10 Drawing Sheets

(56) References Cited

U.S. PATENT DOCUMENTS

| | | | |
|---|---|---|---|
| 6,149,902 | A | 11/2000 | Artavanis-Tsakonas et al. |
| 6,156,331 | A | 12/2000 | Peery et al. |
| 6,165,225 | A | 12/2000 | Antanavich et al. |
| 6,224,893 | B1 | 5/2001 | Langer et al. |
| 6,261,584 | B1 | 7/2001 | Peery et al. |
| 6,287,295 | B1 | 9/2001 | Chen et al. |
| 6,303,379 | B1 | 10/2001 | Selden et al. |
| 6,306,169 | B1 | 10/2001 | Lee et al. |
| 6,361,771 | B1 | 3/2002 | Tao et al. |
| 6,365,149 | B2 | 4/2002 | Vyakarnam et al. |
| 6,387,693 | B2 | 5/2002 | Rieser et al. |
| 6,395,292 | B2 | 5/2002 | Peery et al. |
| 6,410,313 | B1 | 6/2002 | Kasahara et al. |
| 6,413,511 | B1 | 7/2002 | Glorioso et al. |
| 6,455,304 | B1 | 9/2002 | Weigel et al. |
| 6,458,889 | B1 | 10/2002 | Trollsas et al. |
| 6,472,181 | B1 | 10/2002 | Mineau-Hanschke |
| 6,548,249 | B1 | 4/2003 | Anderson et al. |
| 6,635,268 | B2 | 10/2003 | Peery et al. |
| 7,149,587 | B2 | 12/2006 | Wardle et al. |
| 7,897,384 | B2 | 3/2011 | Binette et al. |
| 7,927,599 | B2 | 4/2011 | Story et al. |
| 8,153,117 | B2 | 4/2012 | Binette et al. |
| 8,257,963 | B2 | 9/2012 | Binette et al. |
| 2001/0002392 | A1 | 5/2001 | Heinegard et al. |
| 2001/0014475 | A1 | 8/2001 | Frondoza et al. |
| 2001/0033857 | A1 | 10/2001 | Vyakarnam et al. |
| 2001/0037017 | A1 | 11/2001 | Luyten et al. |
| 2001/0051834 | A1 | 12/2001 | Frondoza et al. |
| 2002/0003727 | A1 | 1/2002 | Hartmann |
| 2002/0006428 | A1 | 1/2002 | Mahmood et al. |
| 2002/0009477 | A1 | 1/2002 | Mahmood et al. |
| 2002/0037279 | A1 | 3/2002 | Vandenburgh |
| 2002/0076810 | A1 | 6/2002 | Radice et al. |
| 2002/0094569 | A1 | 7/2002 | Yu et al. |
| 2002/0110544 | A1 | 8/2002 | Goldberg et al. |
| 2002/0115218 | A1 | 8/2002 | Havenga et al. |
| 2002/0142984 | A1 | 10/2002 | Brigham et al. |
| 2002/0160471 | A1 | 10/2002 | Kisiday et al. |
| 2002/0177224 | A1 | 11/2002 | Madry et al. |
| 2003/0012805 | A1 | 1/2003 | Chen et al. |
| 2003/0036523 | A1 | 2/2003 | Czichos et al. |
| 2003/0064088 | A1 | 4/2003 | Carvalho et al. |
| 2003/0077260 | A1 | 4/2003 | Mineau-Hanschke |
| 2003/0167054 | A1 | 9/2003 | Rosenberg et al. |
| 2003/0181878 | A1 * | 9/2003 | Tallarida et al. |
| 2004/0236192 | A1 * | 11/2004 | Necola Shehada et al. |
| 2005/0036945 | A1 * | 2/2005 | Thomas et al. |
| 2005/0054595 | A1 | 3/2005 | Binette et al. |
| 2005/0191301 | A1 | 9/2005 | Heavner et al. |
| 2006/0030526 | A1 * | 2/2006 | Liu et al. |
| 2006/0292131 | A1 | 12/2006 | Binette et al. |
| 2008/0181954 | A1 | 7/2008 | Binette et al. |
| 2008/0299173 | A1 | 12/2008 | Story et al. |
| 2009/0162386 | A1 | 6/2009 | Story et al. |
| 2010/0114074 | A1 * | 5/2010 | Perry et al. |
| 2011/0171186 | A1 | 7/2011 | Story et al. |

FOREIGN PATENT DOCUMENTS

| | | | |
|---|---|---|---|
| JP | 62198388 | A | 9/1987 |
| JP | 62269697 | A | 11/1987 |
| JP | 2002524083 | T | 8/2002 |
| JP | 2002-534164 | A | 10/2002 |
| JP | 2004-260041 | A | 9/2004 |
| JP | 2006-513013 | A | 4/2006 |
| WO | 96/34955 | | 11/1996 |
| WO | 96/39196 | | 12/1996 |
| WO | 99/11789 | | 3/1999 |
| WO | 0014261 | A1 | 3/2000 |
| WO | 02/074912 | | 9/2002 |
| WO | 03/082302 | | 10/2003 |
| WO | 03/084477 | A2 | 10/2003 |
| WO | 2008/150270 | A1 | 12/2008 |

OTHER PUBLICATIONS

Zamir et. al., (1984) Brain Res., 322: 356-360.
International Preliminary Report on Patentability for Application No. PCT/US2008/064481 dated Dec. 10, 2009. (7 pages).
Anderson et. al., (1990) Cancer Res., 50: 1853.
Arai, et al., "Adenovirus Vector-Mediated Gene Transduction to Chondrocytes: In Vitro Evaluation of Therapeutic Efficacy of Transforming Growth Factor-Beta1 and Heat Shock Protein 70 Gene Transduction," 1997, Journal of Rheumatology, vol. 24, pp. 1787-1795.
Baekkeskov et. al., (1990) Nature, 347: 151-156.
Bakay et. al., (1985) Appl. Neurophysiol., 48: 358-361.
Bartholomew, et al., "Baboon mesencymal stem cells can be genetically modified to secrete hum erythropoietin in vovi," Aug. 2001, Human Gene Therapy, vol. 12, No. 12, pp. 1527-1541.
Baskin et. al., (1994) Life Sci., 54: 471-479.
Bjorklund et. al., (1982) Nature 298: 652-654.
Bohme et. al., (1992) Prog. Growth Factor res., 4: 45-68.
Bohme et. al., (1995)Exp. Cell Res., 216: 191-198.
Bookman et. al., (1998) Semin. Oncol., 25: 381-96.
Carelli (1982) Proc. Natl. Acad. Sci., USA 79: 5392-5395.
Carson et. al., (1998) J. Surg. Res., 75: 97.
Castano et. al., (1991) J. Clin. Endocr. Metab., 73: 1197-1201.
Corvol et. al., (1980) FEBS Lett., 116: 273-276.
Crabb et. al., (1990) J. Bone Mineral Res., 5: 1105-1112.
Dotta et. al., (1992) Endocrinology 130: 37-42.
Downie et. al., (1994) Dev. Biol., 162: 195.
Farnum C E, Lee R, O'Hara K, Urban J P G; Volume increase in growth plate chondrocytes during hypertrophy: the contribution of organic osmolytes. Bone 2002;30(4):574-81.
Fueshko et. al., (1994) Dev. Biol., 166: 331-348.
Gelb et. al., (1990) Endocrinology, 127: 1941-1947.
Gerstenfeld et. al., (1990) Conn. Tiss. Res. 24: 29-39.
Gillard et. al., (1989) Journal Immunol. Methods., 142: 3826-3832.
Golab et. al., (1998) Ann. Oncol., 9: 63.
Greiss et. al., (1993) Biophysical J., 65: 138-148.
Griscelli et. al., (1998) proc. Natl. Acad. Sci., USA 95: 6367.
Grogan, et al. "Engineering Cartilage for Drug Delivery," Institute of Pathology, University of Bern, Murtenstrasse 31, 3010, Ben Switzerland, 2002.
Hahn et. al., (1984) Endocr. Res., 10: 123-138.
Hamamori et. al., (1995) J. Clinical Investigation, 95: 1808-1813.
Hantraye et. al., (1990) Exp. Neurol., 108: 91-1014.
Hantraye et. al., (1992) Proc. Natl. Acad. Sci., USA 89: 4187-4191.
Hearing et. al., (1986) J. Immunol., 137: 379.
Himeno, et al., "Impaired Vascular Invasion of CBFA1-Deficient Cartilage Engrafted in the Spleen," Jul. 2002, Journal of Bone and Mineral Research, vol. 17, No. 7, pp. 1297-1305.
International Search Report and Written Opinion of PCT/US2008/064481 dated Sep. 23, 2008.
Isacson et. al., (1985) Neuroscience 16: 799-817.
Isacson et. al., (1989) Exp. Brain Res., 75(1): 213-220.
Iwamoto et. al., (1993) Exp. Cell Res. 205: 213-224.
Iwamoto et. al., (1993) Exp. Cell Res., 207: 413-420.
Japanese Office Action for Application No. 2010-510425 issued Sep. 18, 2012. (4 pages).
Jorgensen at al. (Immunology Today Trends. Sep. 1998; 19(9): 387-391).
Kanazawa et. al., (1986) Neurosci. Lett., 71: 241-246.
Kato et. al., (1998) Proc. Nat. Acad. Sci., 85: 9552-9556.
Koshiba, T., Clinical Cancer Research, Sep. 2000, V6, p. 3530-3535.
Leboy et. al., (1989) J. Biol. Chem., 264: 17281-17286.
Leboy et. al., (1994) Microscopy Res. and Technique 28: 483-491.
Leibson et. al., (1984) Nature, 309: 799.
Lian et. al., (1993) J. Cellular Biochem., 52: 206-219.
Madry, et al., "Efficient lipid-mediated gene transfer to articular chondrocytes," Feb. 2002, Gene Therapy, vol. 7, No. 4, pp. 286-291.
Maurer-Gebhard et. al., (1998) Cancer Res., 58: 2661.
Okada et al (Biol. Pharm. Bull. 1997. vol. 20, No. 3, pp. 255-258).
Osborne et. al., (1995) Proc. Natl. Acad. Sci., USA 92: 8055-8058.

* cited by examiner

Human articular chondrocytes (HC) encapsulated in alginate in DME/10% FBS or DME/ITS

HC 24 DME 10% FBS

HC 24 DME /ITS

Human ligament cells (ACL) encapsulated in alginate in DME/10% FBS or DME/ITS

ACL DME 10% FBS

ACL DME /ITS

Human fibroblast cells encapsulated in alginate in DME/10% FBS or DME/ITS

FIBROBLASTS DME/10% FBS

FIBROBLASTS DME/ITS

CHONDROCYTE CONTAINER AND METHOD OF USE

RELATED APPLICATION(S)

This application is a divisional of U.S. application Ser. No. 12/123,650, filed May 20, 2008, entitled "Chondrocyte Container and Method of Use," which claims priority under 35 U.S.C. §119 to U.S. Provisional Patent Application Ser. No. 60/941,326, filed Jun. 1, 2007, entitled "Chondrocyte Container and Method of Use," which is incorporated herein by reference in its entirety.

FIELD OF USE

The invention relates to the delivery of therapeutic agents(s) produced via genetically-altered chondrocytes to various treatment sites.

BACKGROUND

The use of various types of biologically active cells as components of implanted devices for the purpose of delivering bioactive agents produced by said cells is well known in the art. Various attempts to devise methods for enhancing the survivability of such implanted cells have ultimately fallen short and require either the vascularization of the implant or a maximum diffusion distance of about 2-3 mm in order to provide nutrients to the cells. These various types of cells include fibroblasts, myoblasts, stem cells, progenitor cells, mature differentiated tissue cells, and undifferentiated cells.

Chondrocytes offer several unique advantages as vehicles for expressing therapeutic agents over other cell types. For example, chondrocytes do not require vascular support, and therefore can readily be used in environments that have a reduced, or non-existent vascularization system. Furthermore, chondrocytes are able to survive in harsh in vivo environments, including low pH and low oxygen surroundings. In addition, there is a reduced likelihood of malignancy due to the anti-angiogenic properties of normal chondrocytes. Chondrocytes also possess an immune privileged property which reduces immune rejection of co-implanted allogenic or xenogenic tissue. Furthermore, chondrocytes are more easily scalable compared to other normal untransformed cell strains. The genetic alteration of chondrocytes to express therapeutic agents for the treatment of pathologies or injuries other than cartilage tissue have been discussed by assignee's co-pending patent applications United States Published Application Nos. 2005/0054595 and 2006/0292131, which are herein incorporated by reference in their entirety.

However, there remains a need for devices and methods capable of delivering a large volume of such genetically-altered chondrocytes to various treatment sites not typically associated with chondroctyes.

SUMMARY

Various embodiments of a device and method for the delivery of therapeutic agent(s) to various treatment sites are provided herein. More specifically, the device includes a housing which defines an internal cell chamber configured to retain a population of genetically-altered chondrocytes. While preventing passage of these chondrocytes, the housing can be configured via a number of exit ports (e.g., semi-permeable membranes) to allow for the controlled release of therapeutic agents produced by these entrapped cells. As will be shown in detail below, the cell chamber can be designed such that the core of the chamber can reside a significant distance from the outer wall of the device (e.g., greater than at least about 1.5 mm). Such a large-scale cell chamber can be utilized in light of the chondrocytes' ability to remain viable even when separated from an external nutrient supply. As shown below, the use of such large-scale delivery devices can significantly increase the amount of therapeutic agent(s) capable of being produced and delivered per delivery device. Various aspects of the device and method are summarized below.

In one aspect, a delivery device is provided which includes a housing having a cell chamber configured to retain a plurality of chondrocytes. For example, the cell chamber can have a length and a diameter wherein each the length and the diameter are at least about 3 mm in dimension. These dimensions provide a device capable of producing and delivering a large amount of therapeutic agent to the treatment site. Additionally, a portion of the housing can be configured to allow for passage of the therapeutic agent(s) produced via the chondrocytes from the cell chamber to the treatment site. For example, the housing can include at least one semi-permeable membrane capable of allowing release of the agents. The membrane can be limited to the distal end of the housing, or multiple membranes can be positioned at various locations along the housing (e.g., extending along each side of the housing). Optionally, the housing, or at least a portion thereof, can be made of a porous metal or ceramic material, such that the cells are retained within the housing but proteins are able to pass through the pores.

The housing can be configured to accommodate the desired mode of delivery, treatment site, type of therapeutic agent to be produced, etc. For example, the housing can include a rigid material, a non-rigid material, or any combination thereof. Further, the distal end of the device can include a pointed (or tapered) section configured to facilitate delivery of the device.

The housing of the delivery device can be configured in various manners to allow for delivery (or replenishment) of the chondrocytes to the delivery device. For example, the device can include a cap which can removably couple to an end of the housing such that removing the cap can allow for introduction of the chondrocytes to the cell chamber. In other embodiments, the housing of the device can include an injection port (e.g., a rubber septum) capable of allowing for injection of additional cells via a syringe. In these embodiment, the chondrocytes can be replenished to the device while the device remains at the surgical site thereby significantly increasing the efficiency and safety of the device.

In other embodiments, the delivery device can include an attachment element (e.g., a suture) coupled to the housing wherein the attachment element is configured to secure the device to tissue/bone at the treatment site. In other embodiments, a radiopaque marker can be disposed on or in the container so as to facilitate positioning and/or locating the device.

In other embodiments, the device can include numerous additional chambers so as to enhance efficiency of the device. For example, in addition to the cell chamber, the device can include an expandable chamber configured to retain a water swellable material wherein the compartments are separated by a piston. In such an embodiment, the introduction of water into the expandable chamber expands the water expandable material thereby forcing the piston to move in a distal direction, and thus forcing an amount of therapeutic agent out of a distal exit port of the cell chamber. Water can be added to the expandable chamber by any number of techniques. For example, the expandable chamber can include an osmotic membrane configured to allow for delivery of water.

In other embodiments, the delivery device can include an auxiliary fluid chamber positioned between the cell chamber and the expandable chamber. Similar to the embodiment described above, the expandable chamber can include a water swellable material capable of driving a piston in a distal direction upon the introduction of water. However, as opposed to directly acting on the cell chamber, in this embodiment, the piston acts on an auxiliary fluid retained within the auxiliary fluid chamber. As will be discussed, the auxiliary fluid (which can include cell nutrients, etc.) can be separated from the cell chamber via a semi-permeable membrane. As such, as the piston moves distally, auxiliary fluid is forced through the semi-permeable membrane and into communication with the condrocytes. Ultimately, the desired therapeutic agent(s) are forced out of an exit port (formed, for example, by another semi-permeable membrane) of the cell chamber, and to the treatment site.

In a further aspect, the device can include a fluid pump and valve system configured to provide a pressurized flow of an auxiliary fluid to the device from an external reservoir. Additionally, the pump and valve system can provide a continuous outflow of desired therapeutics from the device to the treatment site. In some embodiments, the pump can be used to remove cells from the container, and also recharge the container with fresh cells. Also, the pump can be used to infuse the cell chamber of the container with various toxic agents in order to deactive the cells upon completion of the therapeutic regimen.

In some embodiments, the exit port of the delivery device can be in communication with a delivery tube capable of transporting the therapeutic agents from the cell chamber to one or more distant treatment locations. For example, the delivery tube can include numerous branches so as to allow for delivery of therapeutics along each branch and ultimately to various distinct locations.

In another aspect, the delivery device includes a cell chamber configured to retain a plurality of chondrocytes while allowing for the release of a therapeutic agent produced by the chondrocytes. Further, the cell chamber can be sized such that a portion of the chondrocytes are housed a distance of at least about 1.5 mm from an outer wall of the device. As such, the device allows for a large number of cells to be retained a relatively large distance away from an external nutrient source.

In another aspect, a method for delivering a therapeutic agent to a therapeutic site is provided. The method can include disposing a plurality of chondrocytes into a cell chamber of a delivery device. Similar to the embodiments discussed above, the cell chamber can be sized such that a portion of the chondrocytes can be housed within the container at a distance of at least about 1.5 mm from an outer wall of the device (i.e., at least about 1.5 mm from an external source of nutrients). Further, the cell chamber can be configured so as to retain the condrocytes while allowing for the release of a therapeutic agent(s) produced by the chondrocytes. The method further includes delivering the device to a treatment site, and thereafter, delivering the therapeutic agent from the device to the treatment site. In other embodiments, the method can further include suturing the delivery device at the treatment site, and/or injecting additional chondrocytes into the delivery device.

These aspects, and numerous others, will now be discussed in detail below.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present disclosure.

Various exemplary embodiments of devices and methods configured to deliver therapeutic agents produced by genetically-altered chondrocytes are provided herein. More specifically, the devices have an external housing which defines an internal cell chamber. The cell chamber is configured to retain a large-volume of chondrocytes while allowing for the release of therapeutic agents produced by these entrapped cells. As will be seen, the cell chamber is sized such that a core of the chamber can be a relatively large distance away from any external nutrient supply thereby utilizing the enhanced viability of chondrocytes to deliver a large volume of cells, and subsequently a large amount of therapeutic agent to the treatment site. More specifically, the cell chamber can be configured such that at least a portion of the cells entrapped therein can be positioned at least about 1.5 mm away from any external nutrient supply. For example, a tubular cell chamber can be sized so as to have both a length and a diameter of at least about 3 mm thereby requiring any external nutrients to diffuse about 1.5 mm to reach the core of the chamber. As will be described below, the release rate of the therapeutic agent can be controlled by positioning various exit ports (e.g., semi-permeable membranes) at various locations relative to the cell chamber. In some embodiments, the entire housing can include such a semi-permeable membrane. In other exemplary embodiments, the housing can define additional chambers which can interact with the cell chamber to modify the efficiency of the chondrocytes and/or the rate of release of the therapeutic agents. These components and others are now described in detail.

Figures 1A, 1B, 1C:
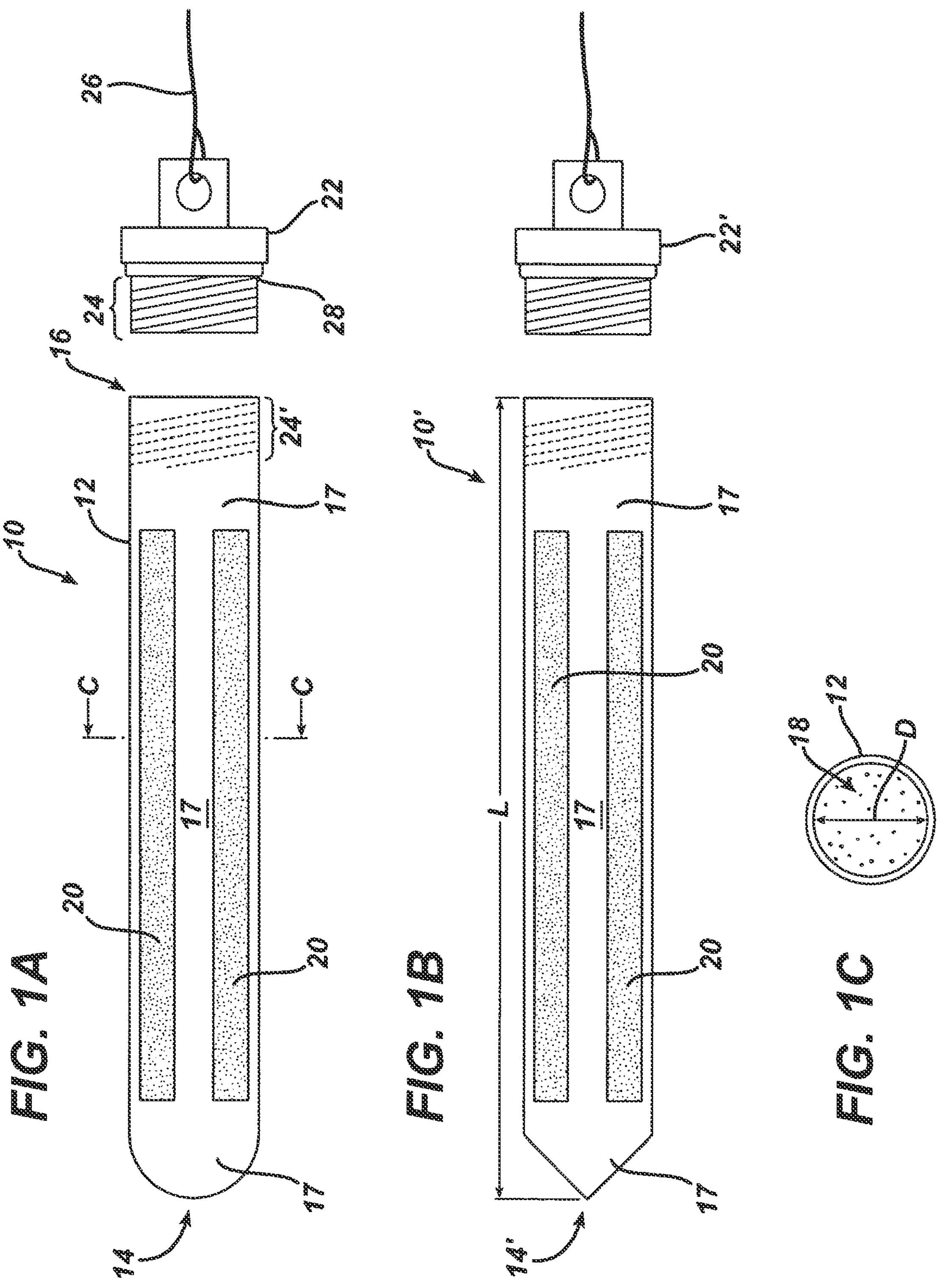
FIG. 1A is a side view of an exemplary embodiment of a delivery device provided herein.
FIG. 1B is an alternative embodiment of the device of FIG. 1A.
FIG. 1C is a cross-sectional view of the embodiment of FIG. 1A taken along line C-C.
Figure 3:
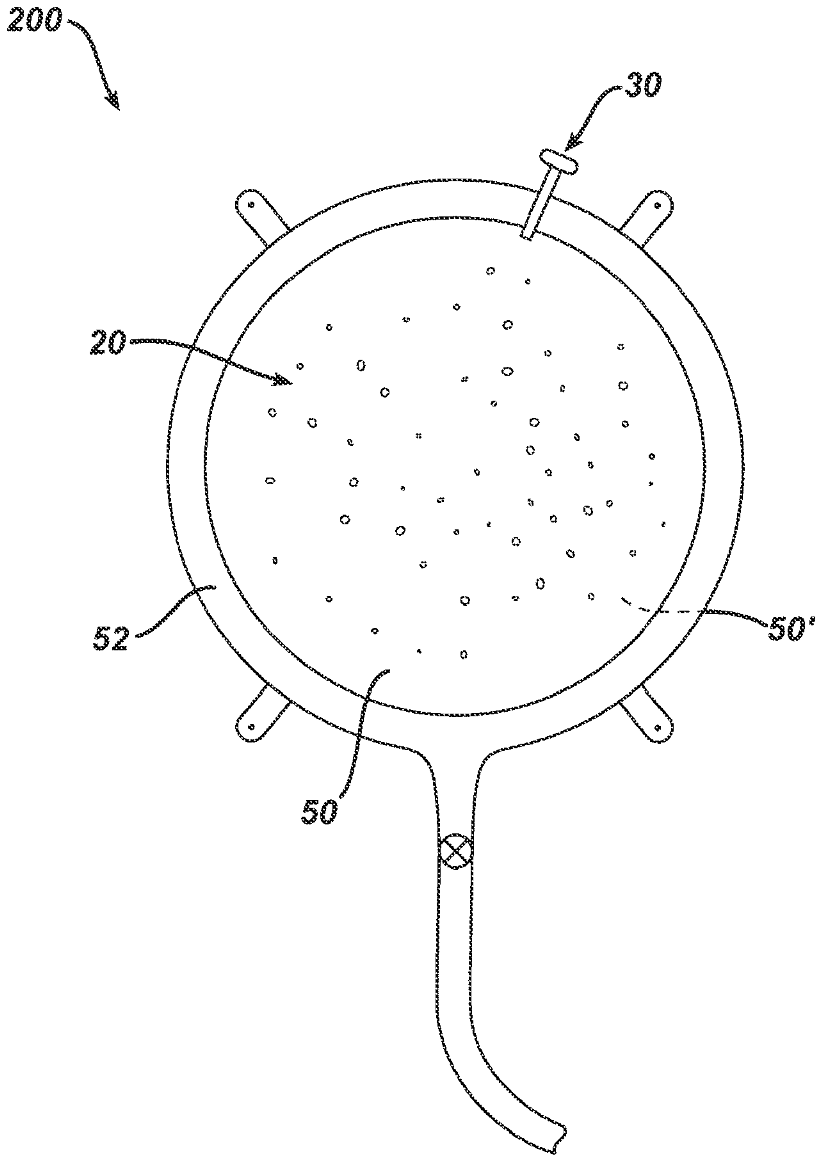
FIG. 3 is a top view of another embodiment of the delivery device.

FIG. 1A provides an exemplary embodiment of a delivery device 10 provided herein. As shown, the device 10 includes a housing 12 having a distal end 14, a proximal end 16, and further defining an internal cell chamber 18 (see FIG. 1C) configured to retain a plurality of genetically-altered chondrocytes. The housing 12 can include a variety of configurations and/or materials so as to optimize delivery and placement of the delivery device 10. For example, the embodiments of FIGS. 1A and 1B provide a substantially tubular housing 12, and the embodiment of FIG. 3 provides a substantially disc-shaped housing 12. Those skilled in the art will appreciate that various such configurations and/or shapes are within the spirit and scope of the present invention.

Additionally, the housing 12 can include both rigid and non-rigid materials which are selected, sized and positioned to optimize delivery of the device, placement of the device at the treatment site, and, as will be explained in further detail below, release rates of the therapeutic agents produced therein. Referring to FIGS. 1A and 1B, the housing can include a rigid frame 17 configured to allow the delivery device 10 to maintain shape during the therapeutic regimen. Also, as shown in FIG. 1B, the rigid frame 17 can allow for a tapered or pointed distal end 14' configured to facilitate insertion and delivery of the device 10'. Those skilled in the art will appreciate that the rigid frame 17 can be formed from various biocompatible, rigid materials. For example, the materials can include various metals, metal alloys, polymers, combination of polymers, or any combination thereof. Additionally, the rigid frame, or at least a portion thereof, can be made of porous materials such as porous metals, ceramics, or polymers to allow the passage of proteins while retaining cells.

Figures 2A, 2B, 2C:
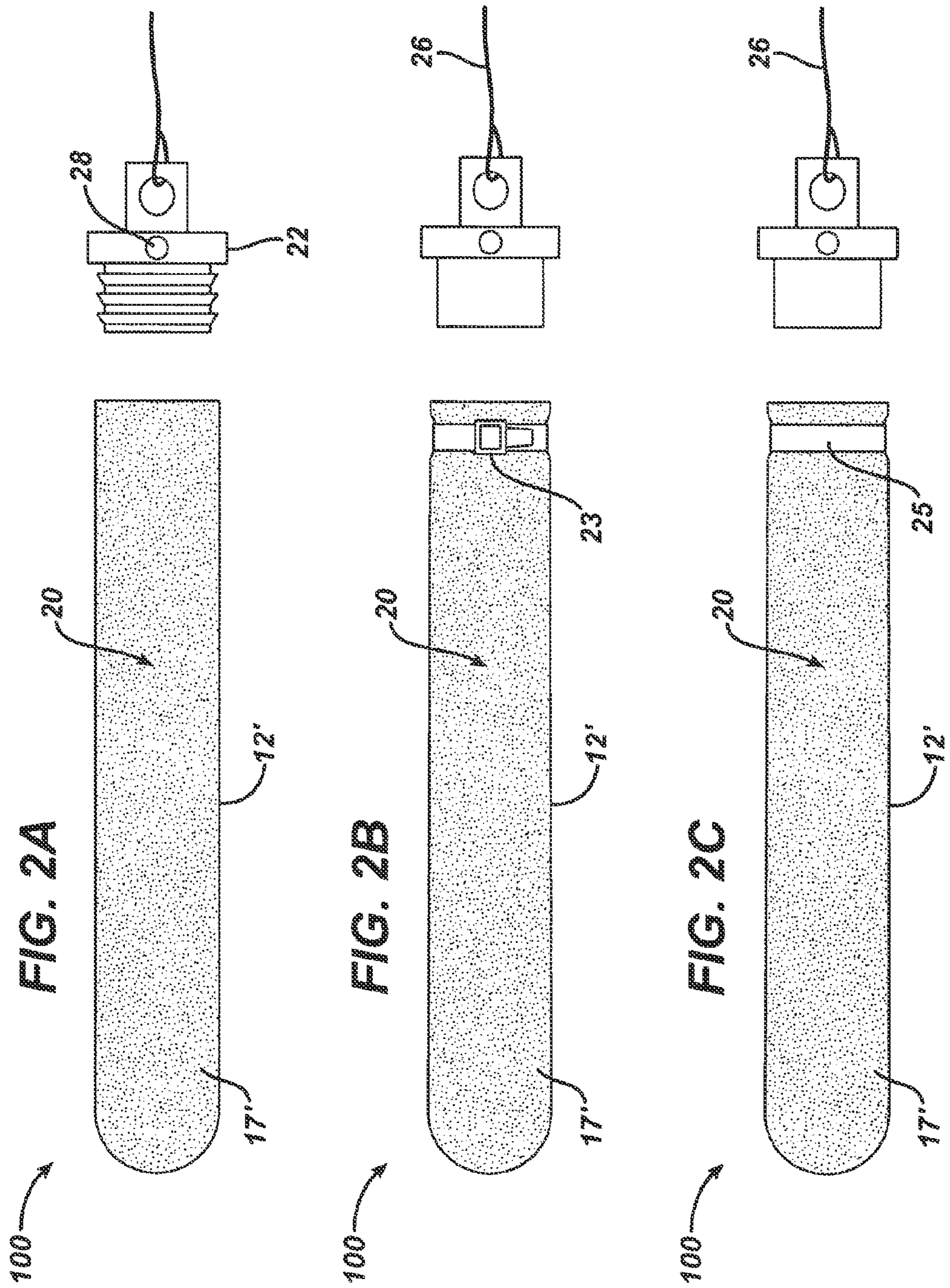
FIG. 2A is side view of another exemplary embodiment of the delivery device.
FIG. 2B is a side view of an alternative embodiment of the delivery device of FIG. 2A.
FIG. 2C is a side-view of another alternative embodiment of the delivery device of FIG. 2A.

Referring to FIGS. 2A-2C, various embodiments of the delivery device 100 can also include a housing 12' having a non-rigid frame 17'. Use of a non-rigid frame 17' can provide a housing 12' capable of changing configuration during delivery of the device 100 to the treatment site, and/or allowing the housing 12' to substantially adopt the shape of the treatment site upon arrival at the site thereby enhancing delivery of the therapeutic agents. As will be apparent to those skilled in the art, the non-rigid frame 17' of the housing 12' can be formed from a wide-range of biocompatible, non-rigid materials. For example, the non-rigid materials can include various polymers configured to prevent the passage of both chondrocytes and the therapeutic agents produced therefrom (i.e., a non-permeable membrane).

The delivery device 10 further includes at least one exit port 20 incorporated into the housing 12, and in communication with the internal cell chamber 18. As will be discussed, the exit port 20 is configured to retain chondrocytes within an internal cell chamber 18 while allowing for the release of a therapeutic agent produced via these entrapped cells. The exit port 20 can be any mechanism configured to allow for such selective release of the therapeutic agents. In an exemplary embodiment, the exit port 20 is a semi-permeable membrane. Those skilled in the art will appreciate that any such membrane 20 capable of retaining genetically-altered chondrocytes while allowing for the release of therapeutic agent(s) produced by these entrapped cells is within the spirit and scope of the present disclosure. For example, the semi-permeable membrane can include a polytetrafluorethylene ("PTFE") membrane with pores ranging from about 0.1 mm to about 0.7 mm. In one embodiment, the pore size is about 0.4 mm to about 0.5 mm. In another embodiment, the pore size is about 0.2 mm.

Exit ports 20 of various sizes, shapes, and/or numbers can be incorporated into the device so as to increase/decrease the release rate of the therapeutic agents. Referring to FIG. 1A, the device 10 includes a first and a second rectangular-shaped exit port 20 extending along a side of the housing 12. FIGS. 2A-2C can include an exit port 20 being incorporated anywhere within the non-rigid housing 12' (indicated generally by an arrow extending towards the housing 12'). For example, the housing 12' can include non-permeable portions and a select area (e.g., the distal tip of the device 100) having a semi-permeable membrane 20 which is configured to retain chondrocytes while releasing the therapeutic agents produced therein. In other embodiments, the entire housing 12' can be formed from the semi-permeable membrane 20.

Looking at other examples, FIG. 3 provides a disc-shaped housing having a top portion 50, a bottom portion 50', and a central ring 52 joining the top 50 and bottom portions 50'. Similar to the embodiments of FIGS. 2A-2C, the entire top 50 and bottom 50' portions of the device 200 can be formed of a semi-permeable membrane 20, or each portion 50, 50' can include a semi-permeable membrane 20 incorporated into a non-permeable material. In other embodiments, the top portion 50 of the device 200 can be formed of a semi-permeable membrane 20, and the bottom portion 50' can be formed of a non-permeable membrane. Those skilled in the art will recognize that any other combination of semi-permeable and non-permeable membranes are also within the spirit and scope of the present disclosure.

Referring to the embodiments of FIGS. 4A-6B, the exit port 20 can be incorporated at the distal tip of the device. Such placement of the exit port 20 can allow for better predictability as to release rate and/or better concentration of the therapeutic agent at the treatment site. Also, use of such a single distal exit port 20 can allow for the therapeutic agent to be delivered directly to a delivery tube 80 for subsequent transport of the agent to various distant locations (as will be discussed below). As will be appreciated by those skilled in the art, embodiments employing a distal exit port 20 can also utilize any number and/or position of additional exit ports 20 and remain within the spirit and scope of the present disclosure.

The various housings discussed above each define an internal cell chamber 18 configured to retain a plurality of genetically-altered chondrocytes. Furthermore, the cell chambers 18 are further in communication with at least one exit port 20 thereby allowing for the release of the therapeutic agents produced via the entrapped cells. As discussed above, the release rate of these therapeutic agents can be modified by changing the number, size, character, pore size, etc. of the exit port 20 in communication with the cell chamber 18. Similar to the above-discussion of the housing, the cell chamber 18 can take various shapes, sizes, and/or configurations. In general, the cell chamber 18 corresponds to the shape of the housing 12 thereby resulting in a cell chamber 18 having a configuration which is tubular (FIGS. 1A-1B), disc shaped (FIG. 3), etc.

As mentioned above, use of chondrocytes allows for a cell chamber 18 configured to retain a large volume of chondrocytes without being required to minimize the diffusion distance between the core of the cell chamber 18 and an external nutrient supply (i.e., an outer wall of the device). More specifically, in an exemplary embodiment, the cell chamber 18 can be sized such that at least a portion of the chondrocytes retained with the cell chamber 18 can be positioned at least about 1.5 mm from an external source of nutrients. For example, referring to FIGS. 1B (showing a length L' of the internal cell chamber 18) and 1C (showing a diameter 'D' of the cell chamber 18), the cell chamber 18 can be sized such that the length (L) and the diameter (D) of the cell chamber 18 are each at least about 3 mm thereby resulting in at least a portion of the cells being at least about 1.5 mm displaced from an external nutrient supply (i.e., the outer housing 12 of the device 10). In other exemplary embodiments, the cell chamber 18 can have a length (L) in the range of from about 100 mm to about 300 mm, and a diameter (D) in the range of from about 3 mm to about 20.0 mm. In other embodiments, the cell chamber 18 can have a length (L) in the range of from about 150 mm to about 250 mm. In another embodiment, the cell chamber 18 has a length (L) of about 200 mm and a diameter (D) of about 10 mm. In another embodiment, the cell chamber 18 has a length (L) in the range of from about 15 mm to about 50.0 mm, and a diameter (D) of from about 10.0 mm to about 30.0 mm.

The delivery device 10 can allow for the introduction of chondrocytes to the cell chamber 18 in a variety of manners. Generally, as introduced to the cell chamber 18, the chondrocytes reside in a gel, gel-like matrix, a liquid suspension, dispersed on a substrate, etc. Those skilled in the art will appreciate that chondrocytes in any such form are within the spirit and scope of the present disclosure. Several examples of such forms which are capable of being utilized are disclosed in assignees' co-pending applications U.S. Published Patent Application No. 2005/0054595 and U.S. Published Patent Application No. 2006/0292131, the entirety of these applications being incorporated herein by reference. These applications also detail the preparation of such genetically-altered chondrocytes. Further, the therapeutic agents and examples of potential treatment sites are detailed below in relation to the methods provided herein.

Referring to FIGS. 1A-1B, the delivery device 10, 10' can include a removable cap 22, 22' which allows for introduction of the chondrocyte cells (as indicated in the FIGS. by dots) to the cell chamber 18. As shown in the embodiment of FIG. 1B, the cap 22' can include an head having a series of flats (e.g., a series of flats forming a hexagon shape) which facilitates grasping of the cap by a tool (not shown). Referring to FIG. 1A, the cap 22 can also include a series of grooves 24 configured to engage a corresponding set of grooves 24' incorporated into an inner wall of the housing 12 thereby allowing the cap 22 to engage or disengage (i.e., screw-on, screw-off) the housing 12. Referring to FIGS. 2A-2C, those embodiments of the device 100 having a housing formed of a non-rigid frame 17' can utilize a compression ring such as a hose clamp 23 or a heat shrink band 25 to engage the cap to the housing 12'. As also shown in the embodiments of FIGS. 1A-1B and 2A-2C, the cap 22 can include additional features such as a radiopaque marker 28 for enhanced visualization of the delivery device 10 once implanted, and/or a suture loop 26 configured to allow the delivery device 10 to be anchored at the treatment site.

Figure 6A:
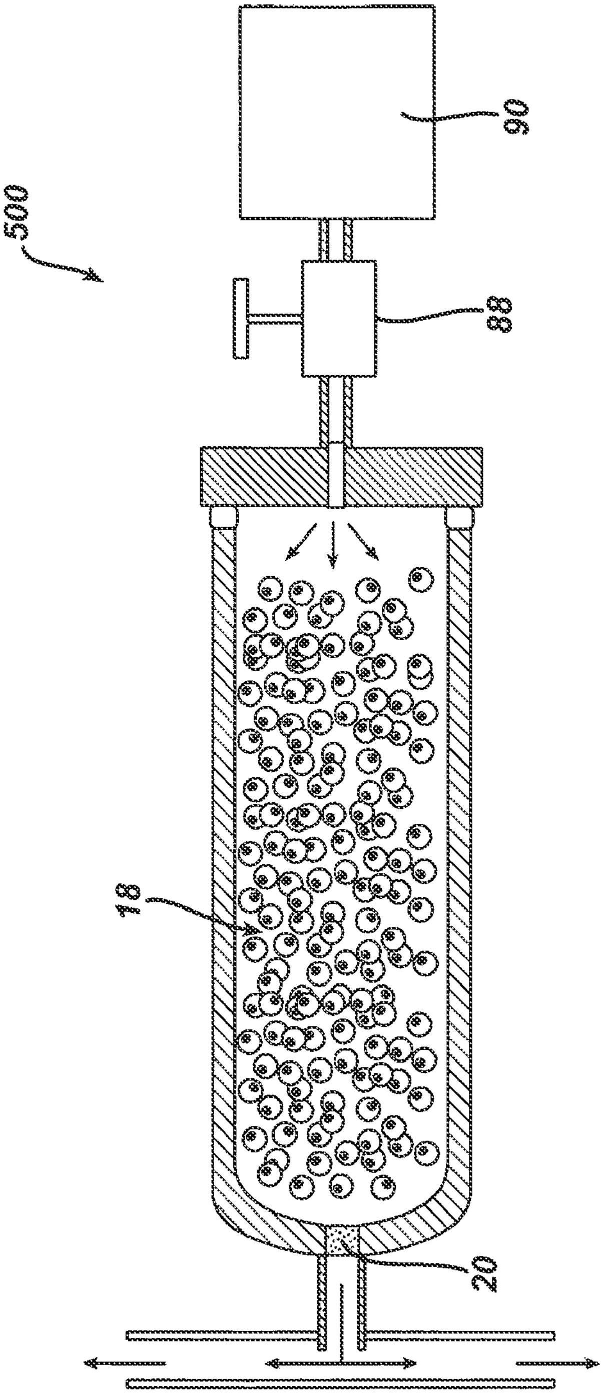
FIG. 6A is a cross-sectional view of another embodiment of the delivery device.
Figure 6B:
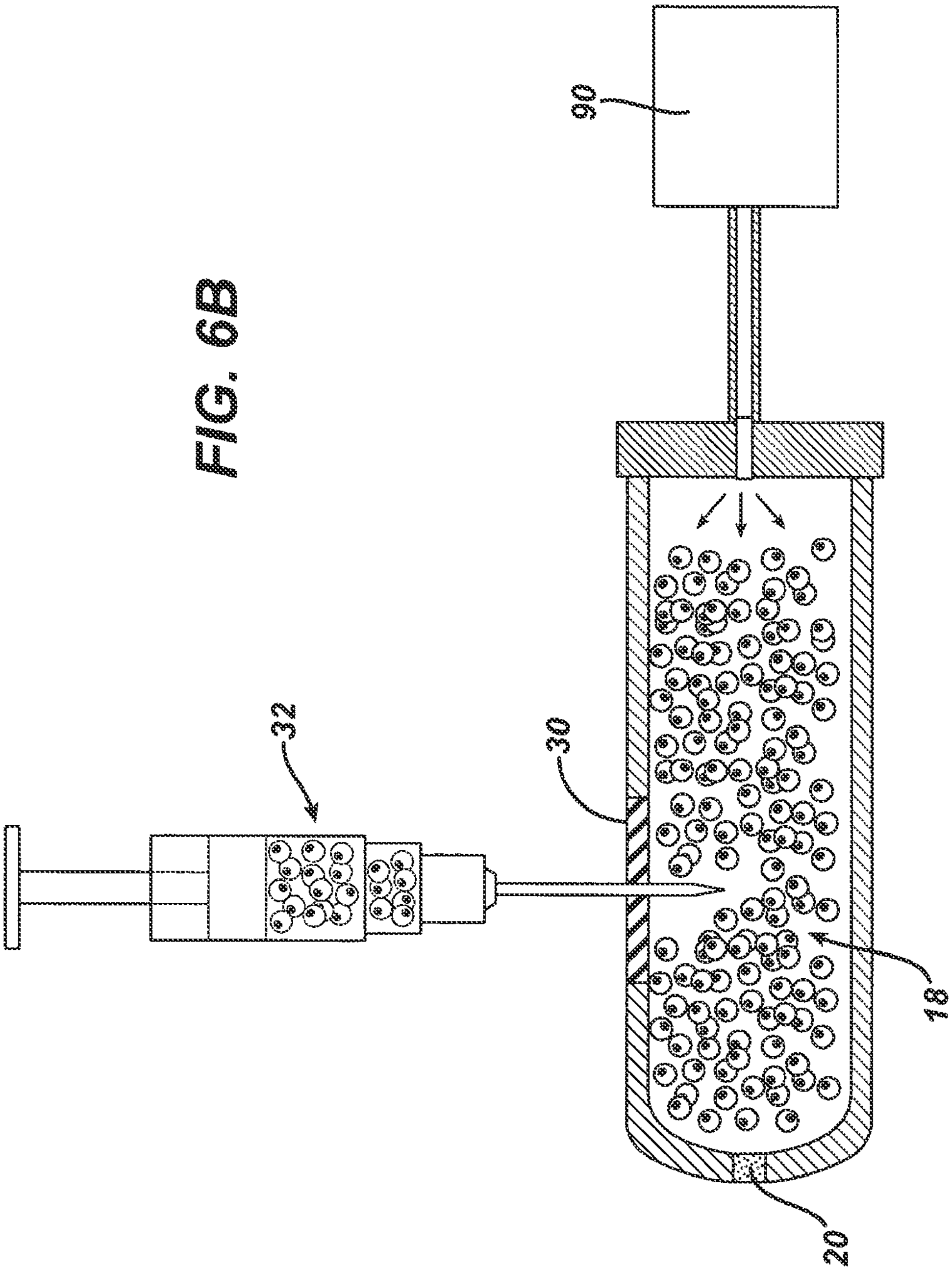
FIG. 6B is a cross-sectional view of an alternative embodiment of the device of FIG. 6A.

In other embodiments, the delivery device can be configured to allow for the introduction of chondrocytes (indicated in the FIGS. by circles which are clearly not to scale) into a sealed cell chamber 18 such as when the device 10 is already positioned at the treatment site. For example, as shown in FIGS. 3 and 6B, the delivery device can include a induction port 30 configured to allow for injection of chondrocytes to the cell chamber 18 via a syringe 32. The induction port 30 can be any mechanism configured to be pierced by the syringe 32 while remaining capable of maintaining a closed environment. For example, the induction port 30 can be a rubber septum incorporated into the housing 12. Those embodiments of the delivery device 10 utilizing such an induction port 30 can be replenished with new chondrocytes without having to remove the device 10 from the treatment site thereby allowing for enhanced efficiency.

Figure 4A:
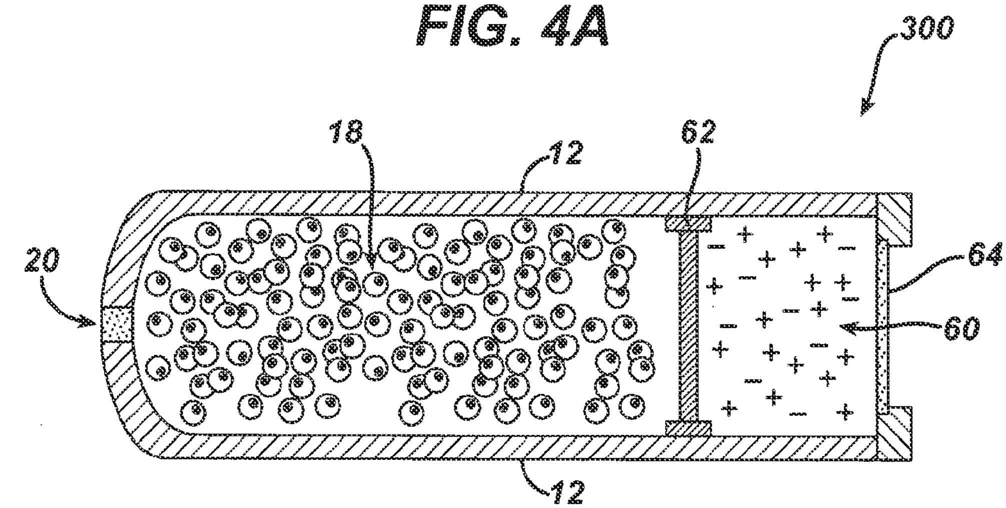
FIG. 4A is a cross-sectional view of another exemplary embodiment of the delivery device wherein a piston element is in a first position.
Figure 4B:
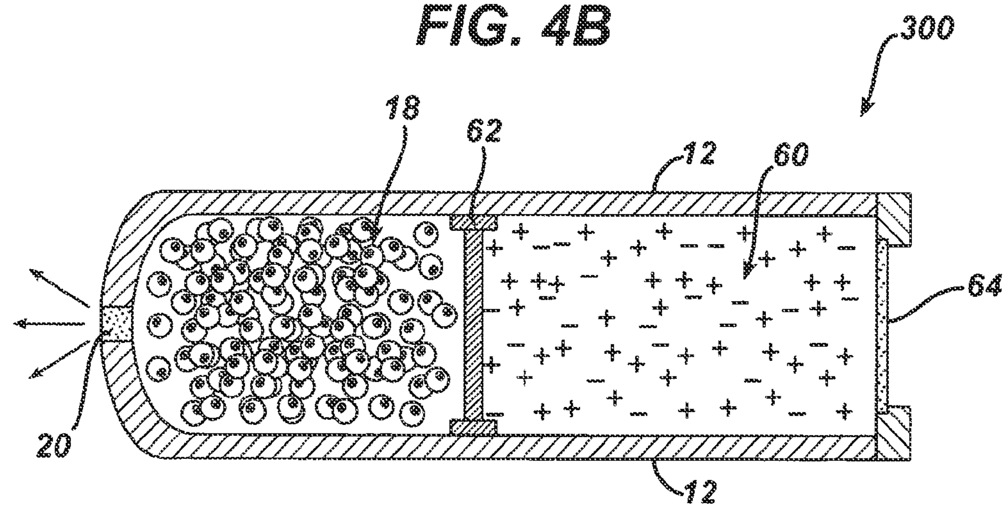
FIG. 4B is a cross-sectional view of the device of FIG. 4A wherein the piston is in a second position.

In other exemplary embodiments, the housing 12 of the device 300 can include various additional chamber(s) so as to control the delivery of the therapeutic agents and/or to provide auxiliary fluids (e.g., cell nutrients, etc.) to the cell chamber 18. Referring to FIGS. 4A and 4B, the housing 12 can define an expandable chamber 60 separated from the cell chamber 18 via a piston 62. The expandable chamber 60 can include a water-swellable agent such that in response to the introduction of water into the expandable chamber 60, the water swellable material expands and drives the piston in the distal direction (as shown in FIG. 4B). As the piston 62 moves distally, the volume of the cell chamber 18 decreases thereby forcing an amount of therapeutic agent out of the distal exit port 20 of the cell chamber 18 (as indicated by a series of arrows).

As will be apparent to those skilled in the art, the water swellable material can be any material cable of expanding in response to the introduction of water. Additionally, as will also be apparent to those skilled in the art, the delivery device 300 can be configured in various manners so as to allow for the introduction of water to the expandable chamber 60. For example, as shown in FIGS. 4A and 4B, the expandable chamber 62 can include an osmotic membrane 64 configured to allow for the introduction of water into the expandable chamber 60.

Figure 5A:
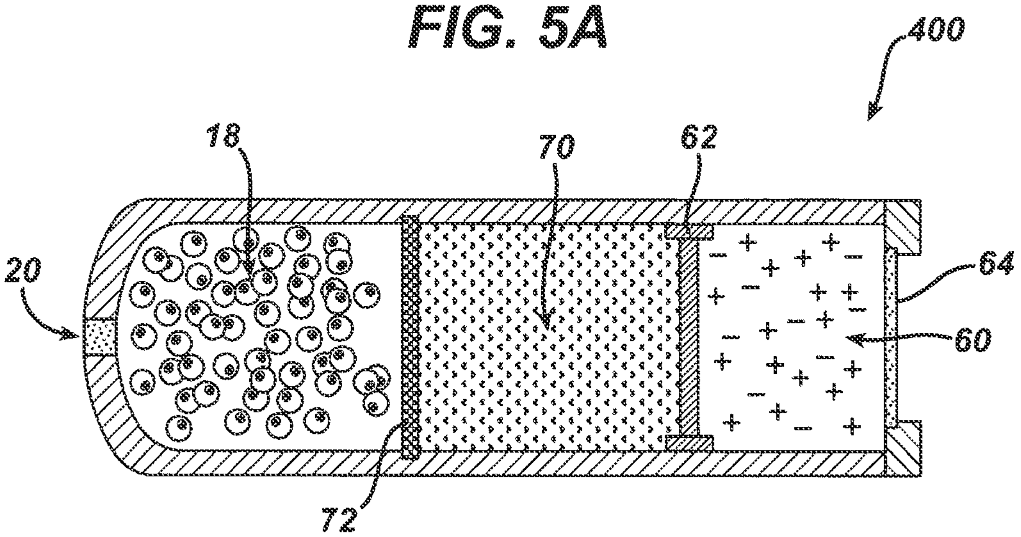
FIG. 5A is a cross-sectional view of another exemplary embodiment of the delivery device wherein a piston is in a first position.
Figure 5B:
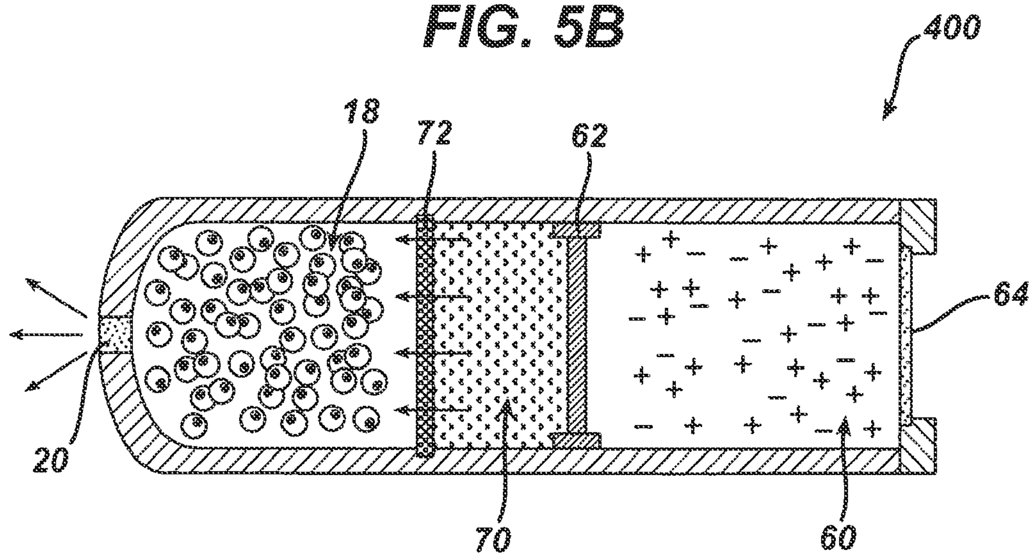
FIG. 5B is a cross-sectional view of the device of FIG. 5A wherein the piston is in a second position.
Figure 5C:
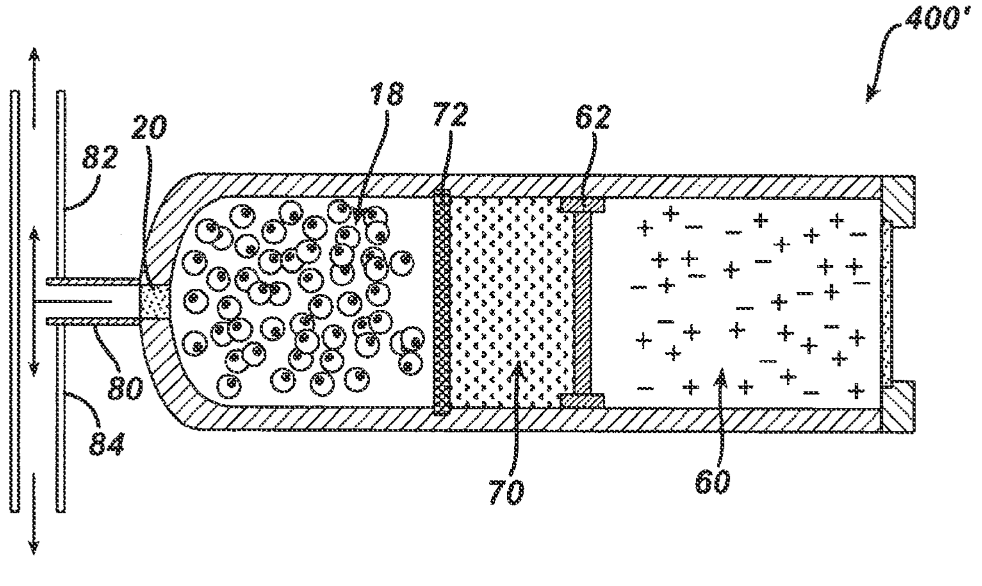
FIG. 5C is a cross-sectional view of an alternative embodiment of the device of FIG. 5A.

In other exemplary embodiments, the delivery device 400 can include an auxiliary fluid chamber 70 configured to retain various auxiliary fluids, and deliver these auxiliary fluids to the cell chamber 18. As will be apparent to those skilled in the art, the auxiliary fluid can be any fluid deemed necessary and/or desirable for a given procedure. For example, the auxiliary fluid can include various cell nutrients, or the auxiliary fluid can be any agent capable of modifying or enhancing chrondrocyte performance. Referring to FIGS. 5A-5C, such the auxiliary fluid chamber 70 can be positioned between the cell chamber 18 and the expandable chamber 60. In such an embodiment, as the expandable chamber 60 expands (as discussed above), the piston 62 is driven in the distal direction. However, in this embodiment, the auxiliary fluid chamber 70 can be positioned adjacent the piston 62. As shown, a semi-permeable membrane 72 can be disposed between the auxiliary fluid chamber 70 and the cell chamber 18 such that the auxiliary fluid is controllably introduced to the population of chondrocytes in response to the expanding water-swellable compartment. As shown in FIG. 5B, introduction of the auxiliary fluid to the cell chamber 18 can force the therapeutic agent(s) out of the distal exit port 20.

In an alternative embodiment, an osmotic pump, such as that of the DUROS device described in U.S. Pat. Nos. 6,287,295; 6,156,331; 6,395,292; 6,261,584; and 6,635,268, the disclosures of which are each incorporated herein by reference in their entirety, could provide for the flow of therapeutic agent. Optimal control could further be provided for by the HAKIM valve mechanism.

Referring to FIG. 5C, other embodiments of the delivery device 400' can be configured to deliver the therapeutic agent(s) from the cell chamber 18 to a distal location (i.e., any location not immediately adjacent the exit port 20). As shown, the distal exit port 20 can be coupled to a delivery tube 80 so as to deliver the therapeutic agent to the distal location. As will be apparent to those skilled in the art, the delivery tube 80 can have any dimensions and/or any length configured so as to be in fluid communication with the exit port 20, and further configured so as to allow for delivery of the therapeutic agent to the desired treatment site. Additionally, the delivery tube 80 can be configured so to deliver the therapeutic agent to various distant locations. For example, in the embodiment of FIGS. 5C and 6A, the delivery tube 80 includes a first branch 82 configured to deliver a portion of the therapeutic agent to a first distal location, and a second branch 84 configured to deliver another portion of the therapeutic agent to a second distal location. Those skilled in the art will appreciate that a delivery tube having one or any additional number of such branches is within the spirit and scope of the present disclosure.

In other embodiments, an external pump 90 and/or valve system 88 can be coupled to the delivery device 500 to provide enhanced control of the delivery of the therapeutic agent from the device 500. Referring to FIG. 6A, an external pump 90 can be coupled to the delivery device 500 via a valve element 88 thereby allowing for continuous pressurized flow of an auxiliary fluid from an external reservoir (not shown). Additionally, introduction of the fluid via the pump 90 can also provide substantially continuous outflow of therapeutic agents from the device 500. Additionally, the pump 90 can be utilized to infuse the cell chamber 18 with various toxic agents so as to deactivate the chondrocytes upon completion of the desired therapeutic regimen. This configuration is somewhat analogous to the HAKIM shunt for hydrocephalitis, except that it is functioning in the reverse direction to actively deliver a fluid into the brain from a reservoir, rather than passively removing a fluid from the brain and draining it into the peritoneal cavity. The valve mechanism of the HAKIM shunt, which is described in U.S. Pat. Nos. 4,332,255, 4,387,715, 4,551,128, 4,595,390, and 4,615,691, the disclosures of each being incorporated herein by reference in their entirety, could be used to remotely adjust the flow of the therapeutic agent transcutaneously, without the need for additional surgery.

In addition to the embodiments discussed above, a method for delivering therapeutic agents to a treatment site is also provided. As described, the device can contain genetically-altered chondrocytes configured to produce and release various therapeutic agents. While the chondrocytes are retained within a large-scale cell chamber of the delivery device, various therapeutic agents can be produced within the device via the chondrocytes and delivered to the treatment site via an exit port in communication with the cell chamber.

The method can include disposing a plurality of chondrocytes into the cell chamber of the delivery device. Similar to the embodiments discussed above, the cell chamber can be sized such that a portion of the chondrocytes can be positioned within the cell chamber at a distance of at least about 1.5 mm from an external source of cell nutrients (e.g., a tubular cell chamber having a length and diameter both of which are greater than at least about 3 mm). Further, the cell chamber can be configured so as to retain the chondrocytes while allowing for the release of a therapeutic agent(s) produced by the chondrocytes. The method further includes delivering the delivery device to a treatment site, and thereafter, delivering the therapeutic agent from the device to the treatment site. In other embodiments, the method can further include suturing the delivery device at the treatment site, and/or injecting additional chondrocytes into the delivery device.

Figures 7A, 7B, 7C:
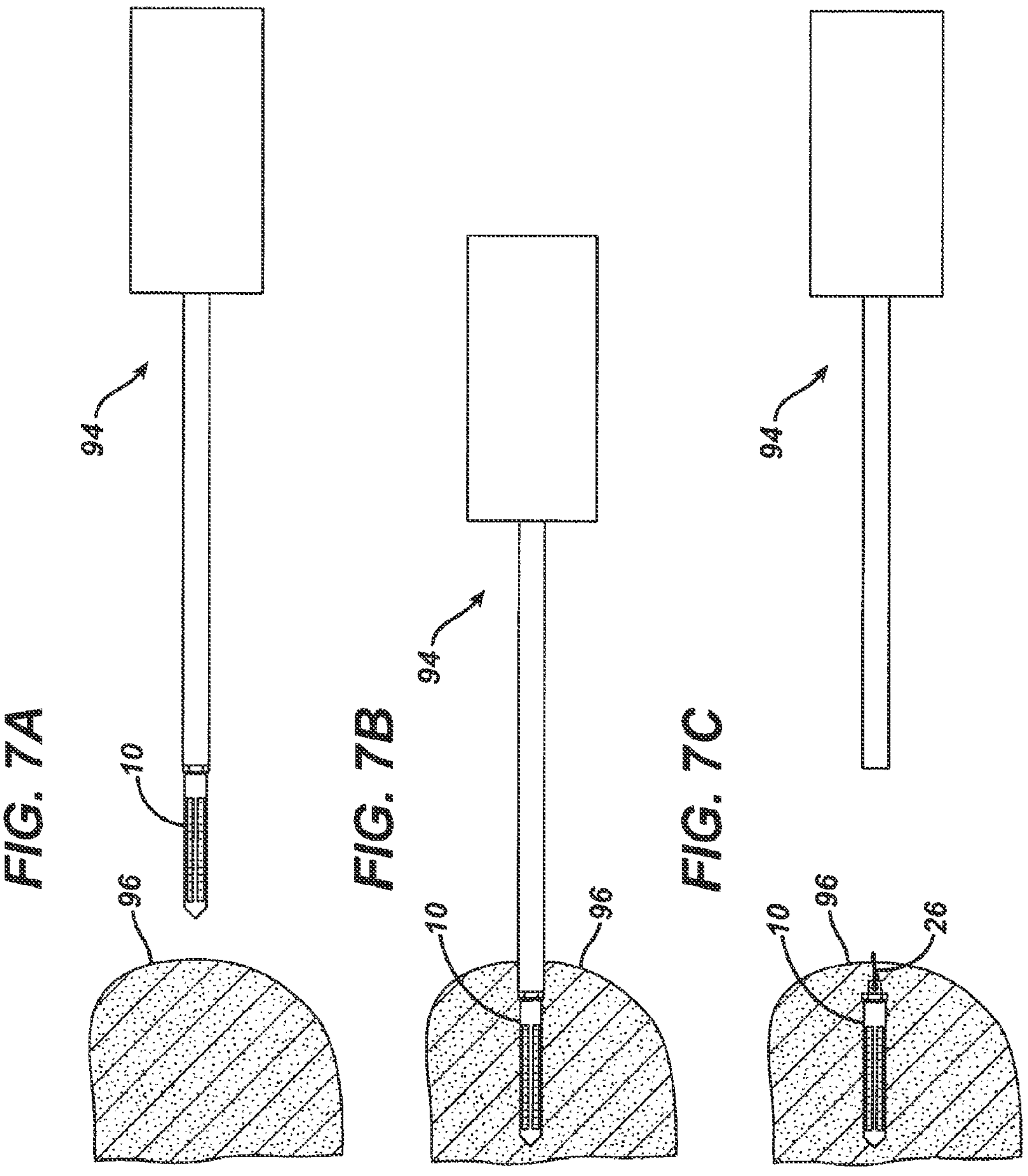
FIG. 7A is side view of an exemplary embodiment of the delivery device being delivered to a treatment site.
FIG. 7B is a side view of the device of FIG. 7A being positioned adjacent the treatment site.
FIG. 7C is a side view of the device of FIG. 7A being secured at the treatment site, and subsequent removal of an insertion tool.
Figure 8A:
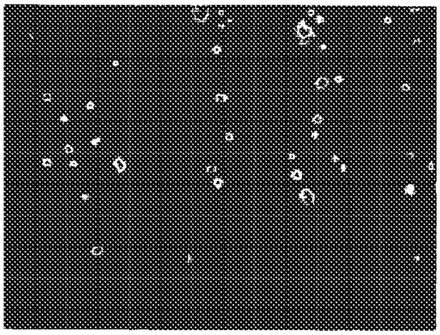
FIG. 8A is a slide showing human articular chondrocytes encapsulated in alginate DME/10% FBS.
Figure 8B:
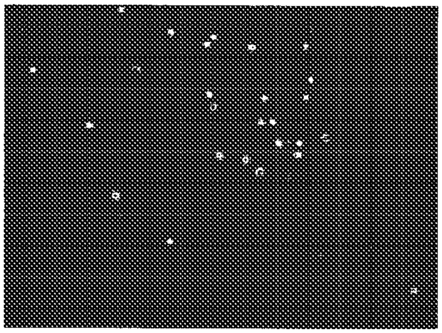
FIG. 8B is a slide showing human articular chondrocytes encapsulated in DME/ITS.
Figure 9A:
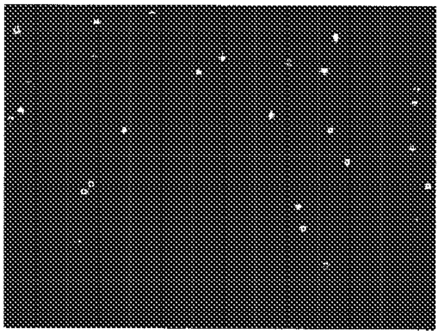
FIG. 9A is a slide showing human ligament cells encapsulated in DME/10% FBS.
Figure 9B:
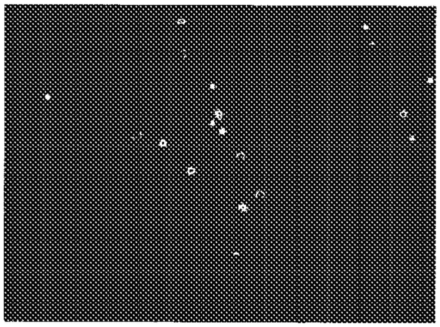
FIG. 9B is a slide showing human ligament cells encapsulated in DME/ITS.
Figure 10A:
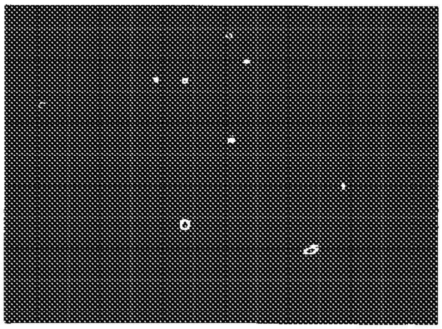
FIG. 10A is a slide showing human fibroblast cells encapsulated in alginate in DME/10% FBS.
Figure 10B:
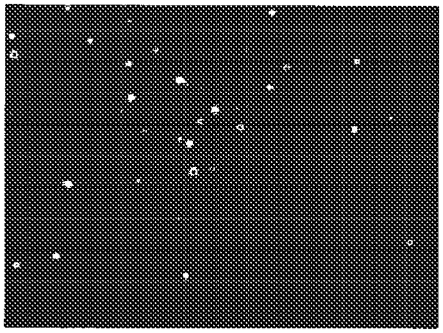
FIG. 10B is a slide showing human fibroblast cells encapsulated in alginate in DME/IT.

FIGS. 7A-7C provides a representation of the device 10 being delivered to the treatment site 96. As shown in FIG. 7A, the device 10 can be mated to an insertion tool 94. As will be apparent to those skilled in the art, various type of insertion tools 94 can be mated to the device 10 in a wide variety of manners thereby allowing the tool 94 to accurately deliver the device 10 to the treatment site 96. Next, FIG. 7B shows the device 10 being positioned at the treatment site 96. As shown, the device can pierce the treatment site 96 (e.g., a tissue) thereby allowing the device to be disposed substantially within the site 96. As shown in FIG. 7C, the device 10 can then be disengaged from the insertion tool 94, and the tool 94 can be removed from the site 96. Once disengaged, the device 10 can be secured to the site 96 via the suture loop 26, and the device can subsequently deliver various therapeutic agent(s) to the site 96.

Various such therapeutic agents can be produced and released via these genetically-modified chondrocytes. In general, the therapeutic agent can be any compound that produces a desired therapeutic effect. For example, the therapeutic agent can be selected from the group consisting of a protein, an agonist or an antagonist of an antibody, an antigen, a hormone, an anti-inflammatory agent, an antiviral agent, an anti-bacterial agent, a growth factor, a cytokine, an oncogene, a tumor suppressor, a transmembrane receptor, a protein receptor, a serum protein, an adhesion molecule, a neurotransmitter, a morphogenetic protein, a differentiation factor, an enzyme, a matrix protein, an extracellular matrix protein, iRNA, RNA, or fragments and peptides thereof. In an exemplary embodiment, the therapeutic agent is a protein such as the Erythropoietin (EPO) protein. Other examples of suitable proteins include, but are not limited to, insulin protein, pro-insulin protein, Remicade, bone morphogenetic protein (BMPs), Transforming growth factor-beta (TGF-beta), Platelet-derived growth factor (PDGF), cartilage derived morphogenic protein (CDMP), and MP-52.

In another embodiment, the therapeutic agent is an antibody, an antibody fragment, or a mimetibody. Examples of a useful mimetibody include but are not limited to EPO mimetibody, Remicade mimetibody, BMP mimetibody, cartilage derived morphogenic protein (CDMP) mimetibody and MP-52. In a preferred embodiment, the antibody is the EPO mimetibody.

In yet another embodiment, the therapeutic agent is a growth factor. In an exemplary embodiment, the growth factors include, but are not limited to, epidermal growth factor, bone morphogenetic protein, vascular endothelial-derived growth factor, insulin-like growth factor (IGF), hepatocyte growth factor, platelet-derived growth factor, hematopoietic growth factors, heparin binding growth factor, peptide growth factors, and basic and acidic fibroblast growth factors. In some embodiments it may be desirable to incorporate genes for factors such as nerve growth factor (NGF), muscle morphogenic factor (MMP), or TGF-beta superfamily, which includes BMPs, CDMP, and MP-52. In yet another embodiment, the therapeutic agent is a receptor. Examples of receptors include, but are not limited to, EPO Receptor, B Cell Receptor, Fas Receptor, IL-2 Receptor, T Cell Receptor, EGF Receptor, Wnt, Insulin Receptor, TNF Receptor.

In other examples, the genetically modified chondrocyte can be used to express a therapeutic agent associated with a blood disorder, e.g., the EPO protein, by delivering the genetically altered chondrocyte to the liver or kidney, or any tissue or organ with a vascular supply to allow EPO to reach the target site or region. Once the EPO protein is expressed, it can enter the circulatory system and bind to, and alter the function of the EPO receptor (EPOR). This in turn will cause a change in the environment associated with the EPO receptor, for example by modifying the signal transduction cascade involving the EPO receptor.

Modification of the tissue may occur directly, for example by over expressing EPO in a target region. Alternatively, modification of a tissue may occur indirectly, for example by the over expressed EPO interacting with an EPOR that leads to changes in downstream signal transduction cascades involving the EPOR. Non-limiting examples of modifications include cell proliferation response, cell differentiation, modifications of morphological and functional processes, under- or over-production or expression of a substance or substances by a cell, e.g., a hormone, growth factors, etc., failure of a cell to produce a substance or substances which it normally produces, production of substances, e.g., neurotransmitters, and/or transmission of electrical impulses.

As mentioned, the delivery device must be initially delivered to the treatment site. The device can be implanted subcutaneously through a simple incision in the skin. Alternatively, the device can be surgically implanted into a target region using standard surgical methods such as open surgery, or more preferably by minimally invasive surgical methods, such as by using a trocar.

In general, the treatment site can be any site wherein a therapeutic agent can provide a therapeutic benefit. In an exemplary embodiment, the treatment site is an atypical chondrocyte environment (i.e., an environment not usually associated with chondrocytes). Examples of an environment not usually associated with chondrocytes include the central nervous system (CNS), which includes the brain and spinal cord. Other examples of environments that are not usually associated with chondrocytes include solid organs. Examples of solid organs include, but are not limited to, the heart, kidney, liver and pancreas. Yet another example of an environment not usually associated with chondrocytes are the reproductive organs. In males, the reproductive organs not associated with chondrocytes are, for example, the testis, vas deferens, and the like. In females, the reproductive organs not associated with chondrocytes are, for example, the uterus, fallopian tubes, ovaries and the like. Other examples of an environment not associated with chondrocytes include the blood, plasma, cerebrospinal fluid (CSF), skin, a subcutaneous pouch, intramuscular and intraperitoneal space.

The following examples are illustrative of the principles and practice of this invention. Numerous additional embodiments within the scope and spirit of the present disclosure will be apparent to those skilled in the art.

EXAMPLES

Example 1

Chondrocytes Contained in Agarose Gel

This example demonstrates the superior ability of chondrocytes to survive in large devices. Three different cell types, chondrocytes, ligament cells and dermal fibroblasts, were encapsulated in large alginate capsules. Cells at a density of $10^6$ cells were encapsulated in cylindrical alginate gel plugs (Alginic acid sodium salt, Fluka #71238) 1 cm diameter×2 cm length and kept in either Dulbecco's Modified Eagle Medium (DME or DMEM; Gibco/Invitrogen #11995-040) with 10% fetal bovine serum (FBS) or DME/ITS (ITS—Insulin, Transferrin, Selenium—Gibco/Invitrogen #51500-056) media for several weeks at 37° C. The cells were then stained with a live/dead dye (Molecular Probes #L3224) that stains the live cells in green (which appear as light spots in FIGS. 8A-10B) and the dead cells in red (which appear as dark spots in FIGS. 8A-10B).

A qualitative visual assessment of the results (see FIGS. 8A-10B) show that the chondrocyte cultures have a higher proportion of live cells (light spots) than dead cells (darker spots) demonstrating their enhanced survivability in large cylindrical constructs.

One skilled in the art will appreciate further features and advantages of the present disclosure based on the above-described embodiments. Accordingly, the present disclosure is not to be limited by what has been particularly shown and described, except as indicated by the appended claims. All publications and references cited herein are expressly incorporated herein by reference in their entirety.

We claim:

1. A delivery device, comprising: a housing having
- a cell chamber configured to retain a plurality of chondrocytes, the cell chamber having a length and a diameter, the length and the diameter each at least about 3 mm;
- a portion of the housing configured to allow passage of a therapeutic agent produced via the chondrocytes;
- an expandable chamber adjacent to the cell chamber, the expandable chamber separated from the cell chamber by a piston element; and
- an auxiliary fluid chamber positioned between the cell chamber and the expandable chamber, the auxiliary fluid chamber configured to house an auxiliary fluid and the auxiliary fluid chamber separated from the cell chamber via a semi-permeable membrane.

2. The delivery device of claim 1, wherein the housing comprises a rigid material.

3. The delivery device of claim 2, wherein the housing further includes at least one semi-permeable port configured to allow passage of the therapeutic agent.

4. The device of claim 1, further comprising a cap removably coupled to an end of the housing.

5. The delivery device of claim 1, further comprising a suture loop coupled to the housing, the suture loop configured to engage the device to a tissue.

6. The delivery device of claim 1, further comprising a radiopaque marker.

7. The delivery device of claim 1, wherein the expandable chamber houses a water swellable agent configured to supply a force to the piston in response to an input of water.

8. The delivery device of claim 7, wherein the expandable chamber further includes a proximal end having an osmotic membrane thereby allowing for the input of water to the expandable chamber.

9. The delivery device of claim 1, wherein the auxiliary fluid includes cell nutrients.

10. The delivery device of claim 1, wherein the auxiliary fluid includes an agent capable of modifying an aspect of chondrocyte performance.

11. The delivery device of claim 1, further comprising a delivery tube in communication with the housing such that the therapeutic agent can be delivered from the cell chamber to a distant location.

12. The delivery device of claim 1, further comprising an auxiliary fluid reservoir in communication with the cell chamber via a valve, the valve configured to allow or prohibit the introduction of the auxiliary fluid to the cell chamber.

13. The delivery device of claim 12, further comprising a pump in communication with the fluid reservoir.

14. The delivery device of claim 1, further comprising an entrance port configured to allow for the introduction of chondrocytes to the cell chamber.

15. The delivery device of claim 14, wherein the entrance port is a rubber septum.

16. The delivery device of claim 1, wherein the housing is at least partially made from a porous material selected from the group consisting of metals, ceramics, and polymers.

17. A delivery device, comprising:

a cell chamber configured to retain a plurality of chondrocytes, the cell chamber further configured to allow for the release of a therapeutic agent produced by the chondrocytes, wherein the cell chamber is sized such that a portion of the chondrocytes are a distance of at least about 1.5 mm from an outer wall of the device;

an expandable chamber adjacent to the cell chamber, the expandable chamber separated from the cell chamber by a piston element; and an auxiliary fluid chamber positioned between the cell chamber and the expandable chamber, the auxiliary fluid chamber configured to house an auxiliary fluid and the auxiliary fluid chamber separated from the cell chamber via a semi-permeable membrane.

* * * * *